United States Patent [19]
Walters et al.

[11] Patent Number: 5,007,291
[45] Date of Patent: Apr. 16, 1991

[54] ULTRASONIC INSPECTION APPARATUS WITH CENTERING MEANS FOR TUBULAR MEMBERS

[75] Inventors: William T. Walters, La Marque; Carroll R. Thompson, Woodlands, both of Tex.

[73] Assignee: Scan Systems, Inc., Channelview, Tex.

[21] Appl. No.: 417,439

[22] Filed: Oct. 5, 1989

[51] Int. Cl.$^5$ .................... G01N 29/20; G01N 29/26
[52] U.S. Cl. ........................... 73/640; 73/637; 73/638; 73/641; 73/622; 73/624; 226/176; 226/177
[58] Field of Search .............. 73/637, 638, 640, 641, 73/622, 624; 226/176, 177

[56] References Cited

U.S. PATENT DOCUMENTS

| | | | |
|---|---|---|---|
| 3,455,150 | 3/1966 | Wood | 73/71.5 |
| 3,791,564 | 8/1972 | Hugonin | 226/19 |
| 4,404,853 | 3/1981 | Livingston | 73/622 |
| 4,596,953 | 4/1983 | Nagasaka et al. | 324/242 |
| 4,718,277 | 12/1985 | Glascock | 73/622 |
| 4,726,231 | 2/1988 | Tretout et al. | 73/644 |
| 4,738,139 | 4/1988 | Blessing et al. | 73/644 |
| 4,774,842 | 2/1986 | Kollar et al. | 73/640 |
| 4,862,748 | 9/1989 | Woodmansee | 73/644 |

FOREIGN PATENT DOCUMENTS

| | | | |
|---|---|---|---|
| 1259579 | 1/1968 | Fed. Rep. of Germany | 73/622 |
| 1040242 | 8/1966 | United Kingdom | 73/622 |
| 2059587 | 4/1981 | United Kingdom | 73/622 |

OTHER PUBLICATIONS

The Radio and Electronic Engineer, vol. 41, No. 5 (May 1971), pp. 213-222 Authors G. H. Kyte et al., Title-A High Speed Ultrasonic Testing Machine for Tubes.

*Primary Examiner*—Hezron E. Williams
*Assistant Examiner*—Craig Miller

[57] ABSTRACT

Pipe inspection apparatus comprising transducers for transmitting pulsed beams of ultrasonic energy longitudinally, transversely and obliquely into the wall of the pipe for detection of flaws. The apparatus includes a motor driven chuck 18 for rotating the transducers about the a pipe P and motor driven roller 12 for axial movement of the pipe whereby the transducers move in a helical scanning path. A control system 60 maintains the axes of the pipe and circle array of transducers in coincidence and with hydraulic controls 80 maintains each transducer at fixed distance to the pipe for sonically coupling thereto by a flowing liquid whereby a shear wave is generated by each beam in the tubular wall. The transducers comprise multiple pairs, the members of which are diametrically opposed and transmit in opposite directions, for transmitting longitudinally at angles of 12°, 27° and 42° to the pipe axis both clockwise and counterclockwise with one transducer of each pair disposed to transmit forward and the other reverse. For longitudinal flaws, one transducer of a pair transmits transverse clockwise and the other transverse counterclockwise. All transducers which transmit in a given direction are arrayed in the axial direction of the pipe. Pulsers 103, 161 simultaneously and repetitively energize and de-energize all forward transmitting transducers and after each such transmission pulsers 105, 162 simultaneously and repetitively energize and de-energize all reverse transducers. Reflection signals of predetermined strength are recorded and activate an alarm. A compressional wave transducer for determining wall thickness is included.

6 Claims, 7 Drawing Sheets

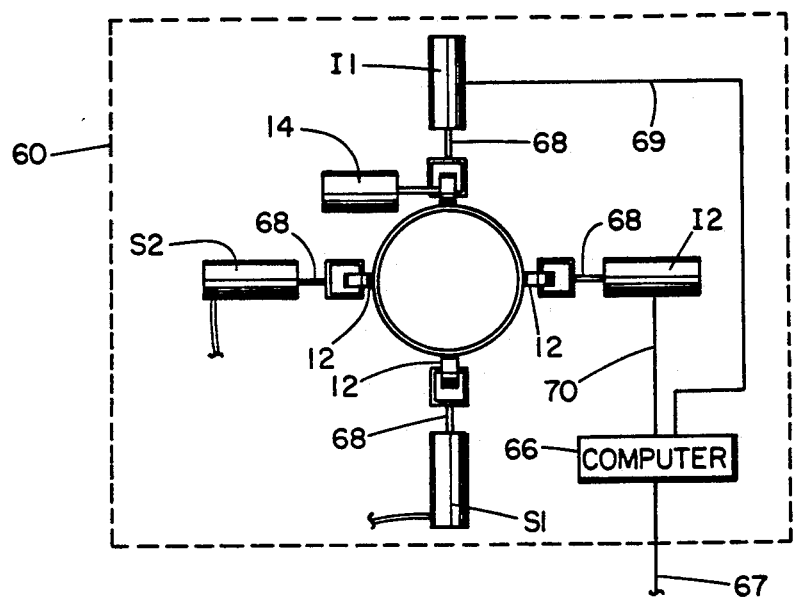
FIG. 4A
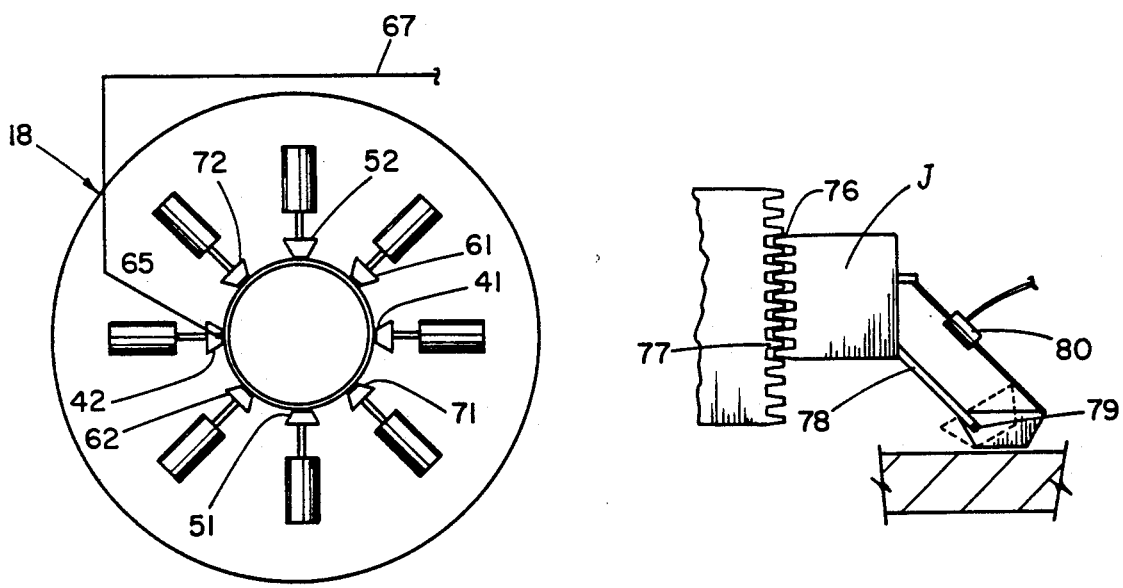
FIG. 4B
FIG. 4C

5,007,291

ULTRASONIC INSPECTION APPARATUS WITH CENTERING MEANS FOR TUBULAR MEMBERS

FIELD OF THE INVENTION

This invention relates to a system for the ultrasonic testing of tubular members, and in particular, to an arrangement and method of operation of transducer arrays for transmitting sonic beams into the wall of a tubular member to detect flaws therein.

BACKGROUND OF THE INVENTION

One of the most widely used techniques for the non-destructive testing and inspection of tubular members, such as steel pipe, involves the use of sonic beams of ultrasonic frequencies. Typically, the apparatus employed in such techniques includes a piezoelectric crystal or crystals, each of which produces ultrasonic vibrations in response to the application of a voltage. When inspecting a tubular member or pipe for internal flaws, such techniques predominantly rely on the method wherein a crystal is maintained in a position relative to the pipe surface to transmit a short duration sonic wave pulse of beamed energy into the wall of the pipe at an angle such that a flaw or discontinuity in the pipe will cause the waves to be reflected back and produce a voltage response in the crystal. The crystal is de-energized immediately following the pulsed emission of a sonic wave so that reflected waves can be received during the de-energized periods to produce a corresponding electrical signal which may be analyzed for determining the nature and location of flaws. U.S. Pat. No. 4,217,782 and U.S. Pat. No. 4,718,277 each disclose an ultrasonic inspection device for inspecting pipe which employs a first pair of transducers for transmitting sonic beams longitudinally into the pipe wall to detect defects which extend transversely of the pipe and a second pair of transducers for transmitting sonic beams into the pipe wall in the transverse direction in order to detect defects which extend in the longitudinal direction of the pipe. Two additional pairs of transducers are provided for transmitting sonic beams through the pipe wall obliquely with respect to its axis so as to detect flaws which extend at an angle intermediate the longitudinal and transverse. The transducers in each pair transmit their sonic beams in opposite directions, so that flaws which are canted in the direction of sonic beam travel from one of the pair of transducers and likely to weakly reflect the beam or be substantially invisible thereto, will provide a strong reflection of the other transducer's sonic beam traveling thereto from the opposite direction. It is also the usual practice that the pipe is scanned by rotating it about its longitudinal axis while simultaneously moving the pipe in its lengthwise direction past the array of transducers or by moving the transducers in carriages along the length of the pipe as the pipe is rotated.

SUMMARY OF THE INVENTION

The invention is an apparatus for the non-destructive testing and examination of a tubular member. The apparatus comprises a circular array of ultrasonic transducers positioned adjacent to and in non-contacting relation with the tubular member for transmitting pulsed beams of sonic energy longitudinally, transversely and obliquely into the wall of the tubular member for the detection of structural flaws therein. The apparatus includes means for rotation of the transducers about the tubular member and simultaneous axial movement of the tubular member through the center of the array whereby the transducers are moved in a helical scanning path relative to the outer surface of the tubular member. Means are also provided for automatically maintaining each transducer at a fixed distance to the tubular member and orientation such that a shear wave is generated by each sonic beam in the tubular wall directed at a refracted angle of approximately 42° from the normal for generating flaw-induced reflections for detection. The transducers are mounted on an annular support member rotatable about its axis and that of the tubular member which is passed therethrough. The transducers comprise multiple pairs, the members of which are mounted in diametrically opposed positions and transmit in opposite directions. Multiple pairs are provided for transmitting in the longitudinal direction and other multiple pairs for transmitting at oblique angles of 12°, 27° and 42° to the tubular member axis in both the clockwise and counterclockwise directions with one transducer assembly of each pair disposed to transmit forward and the other transducer assembly disposed to transmit in the reverse direction. For the detection of longitudinally extending flaws, one transducer of a pair transmits in the transverse clockwise direction and the other in the transverse counterclockwise direction. All transducers which transmit in a given direction are mounted in a transducer holder in spaced array in the axial direction of the tubular member and each of their sonic beams is coupled to the tubular member by a flowing column of liquid medium supplied to the transducer holder.

The apparatus further includes means comprising a source of clock pulses and an electronic switch for simultaneously and repetitively energizing and de-energizing all forward transmitting transducers to transmit beams of shear wave sonic energy and to receive reflections thereof and after each such transmission simultaneously and repetitively energizing and de-energizing all reverse transmitting transducers. Electrical signals which are transducer-generated upon receipt of a sonic reflection are recorded by a recorder means and used to activate an adjustable audible alarm.

BRIEF DESCRIPTION OF THE DRAWINGS

FIG. 4a is a schematic diagram of the control system for automatically maintaining the transducers a fixed distance from the pipe as the pipe is scanned by the transducers;

FIG. 4b is a schematic diagram illustrating the orientation, with respect to a pipe to be inspected, of the transducer holders of the invention;

FIG. 4c is a fragmentary view showing attachment of a transducer holder to a chuck jaw;

Figure 1:
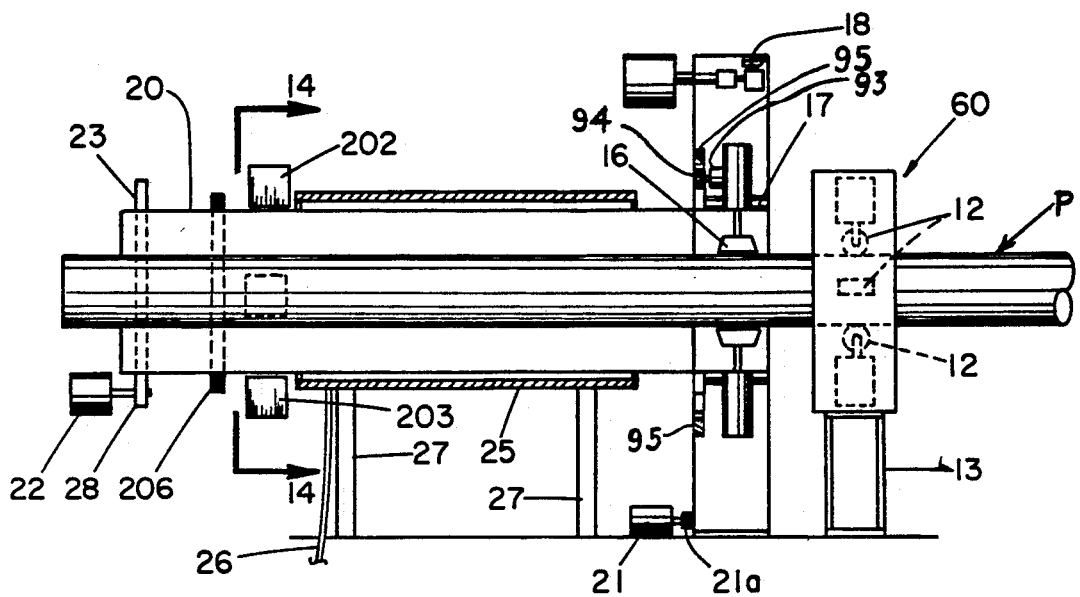
FIG. 1 is a side view, partly in section, of a pipe inspection station illustrating a preferred form of the transducer assembly of the invention in operative position with respect to a pipe to be inspected.

Referring more particularly to the drawings, there is shown in FIG. 1, a pipe inspection station 60 wherein a pipe P to be inspected is transported to an array of transducers which are positioned and adapted to transmit beamed sonic pulses into the wall of the tubular member to detect flaws located therein using a pulse-echo method wherein the transmit time of a reflected sonic pulse is an indicator of the location of a flaw defect.

The pipe P is supported on a plurality of rollers 12 mounted on an upright support 13. The rollers 12, preferably four in number, are arranged in equiangular circumferential spacing about the pipe P and one of the rollers is rotatably driven by a motor 14, shown schematically in FIG. 4a, to drive the pipe P in longitudinal axial movement past an array of ultrasonic transducers mounted in transducer holders or shoes 16. The transducer holders 16 are eight in number, each mounted on a different jaw of an eight jaw chuck 18, in equiangular spacing about the circumference of the pipe. The chuck 18 is mounted on one end of a hollow barrel 20 in concentric coaxial alignment therewith and on a bearing assembly 17 so as to be independently rotatable thereon. Rotation of the chuck is effected by a drive motor 21 through a gear connection 21a. The barrel 20 is rotatable by a drive motor 22 through an appropriate gear drive mechanism 23 and is adapted for rotation within an outer barrel 25 supported on a thin film of water. The water is supplied to the annulus between the inner wall of the outer barrel and the outer wall of the inner barrel by a suitable water supply pump (not shown) through a conduit 26. The thin film of water provides a water bearing between the outer barrel 25 which is held in fixed position on appropriate supports such as upright supports 27 and the inner barrel 20 which rotates therein.

As the inner barrel is rotated, the chuck 18 and transducer mounts 16 are also rotated about the pipe P which is driven in longitudinal axial movement therebetween. Accordingly, the transducers in the mounts 16 move in a helical scanning path about the surface of the pipe P.

The ultrasonic transducers employed in the present invention are of conventional piezoelectric crystals, of the type adapted to transmit a beam of high frequency sonic energy. The transducers are mounted in transducer holders or shoes such as the holder 71 illustrated in FIGS. 6, 7 and 8. As will hereinafter be described the holders are maintained in a position spaced one-eighth inch from the surface of the pipe to be inspected.

Figure 2:
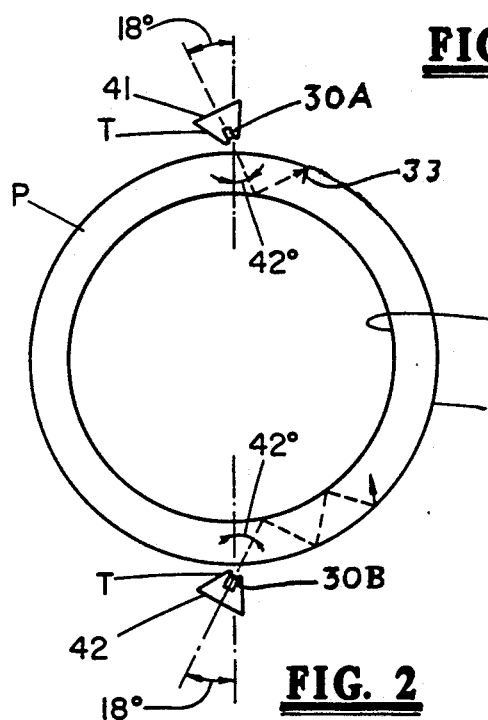
FIG. 2 is a cross section of a pipe, enlarged to show the paths of ultrasonic shear waves transmitted to the pipe by an opposing pair of ultrasonic transducers.

The transducers employed in the invention are each adapted to transmit a pulsed beam of sonic energy upon the energizing application of a high voltage pulse and when deenergized to generate a voltage signal in response to the receipt of a sonic signal. The transducers selected for the detection of flaws in the pipe wall are adapted to produce ultrasonic waves for coupling through a flowing column of liquid medium to the pipe where they are transmitted in the shear mode through the solid portion of the pipe wall between its cylindrical inner and outer surfaces. However, one of the transducers is used for measurement of the pipe wall thickness and is adapted to produce ultrasonic waves which are coupled through a flowing column of liquid to the pipe where they are transmitted in the longitudinal mode. Shear waves have an angle of refraction as shown in FIG. 2, and are repeatedly reflected between the inner and outer surfaces (35,36) of the pipe to eventually dissipate or to be reflected back to the transmitting transducer T in the event of an encounter with a flaw or discontinuity, such as an inclusion or crack 33 in the pipe wall. All of the shear wave generating transducers in the invention are positioned to transmit a cylindrical beam to the convex outer surface of the pipe at an incident angle inclined eighteen degrees from the perpendicular. As will hereinafter be described, the sonic energy is coupled to the pipe by a flowing column of water and shear wave energy is refracted at an angle of 42° from the perpendicular radial direction. While an incident angle of 18° is preferred, an incident angle which results in shear wave propagation could be used.

Figure 3:
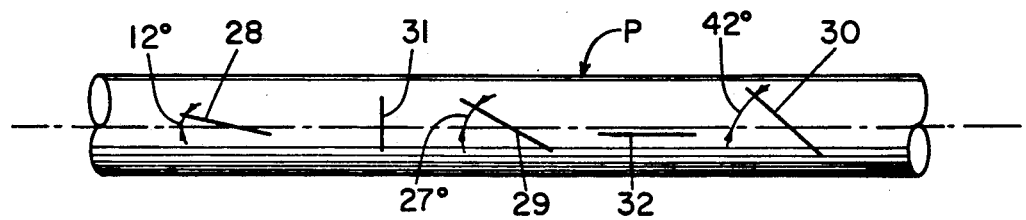
FIG. 3 is a fragmentary view of a section of pipe illustrating the various orientations of flaws in the pipe.

FIG. 3 is an illustration of the orientation of defects or flaws in a pipe or other tubular member which are ideally situated for detection by the invention. Flaws 28,29,30 in the pipe P are disposed obliquely with respect to the axis of the pipe at angles of 12°, 27° and 42°, respectively. The flaw 31 is a transverse flaw and flaw 32 is a longitudinal flaw extending in the direction of the longitudinal axis of the pipe.

For the detection of flaws which extend in the longitudinal direction of the pipe, a single pair of diametrically opposed transducers are employed. Each transducer is adapted to transmit a sonic beam into the wall of the tubular member for travel therein between its inner and outer cylindrical surfaces and in a direction transverse to the longitudinal axis of the tubular member. Since a given defect may be invisible to a transducer looking at it from one direction, one transducer is disposed to transmit its sonic beam in a clockwise direction while the other transmits in a counterclockwise direction. One of the transducers 30A, as shown in FIG. 2, is mounted in a transducer shoe 41 and is disposed to transmit a beam of ultrasonic energy transversely with respect to the pipe in the clockwise direction. The other transducer 30B of the pair is mounted in a transducer shoe 42 and is disposed to transmit a beam of ultrasonic energy transversely in the counterclockwise direction.

For the detection of defects which extend in the transverse direction of the pipe, three pairs of transducers are employed. One transducer of each pair is positioned to transmit its beam of ultrasonic energy forward in the axial direction of the pipe whereas the other transducer of the pair is positioned to transmit in the reverse axial direction. All the forward transmitting transducers of the three pairs are mounted in one transducer holder 51 and the reverse transmitting transducers are mounted in a transducer holder 52 disposed diametrically opposed to the holder 51. The relative locations of the transducer shoes 41,42 and 51,52 are shown in FIG. 4b and the fragmentary perspective view of FIG. 5. As mounted in a shoe, the transducers are uniformly spaced in the axial direction of the pipe and provide an effective scan length of at least .7 inch for each revolution of the transducer with respect to the pipe.

For the detection of flaws which extend at angles intermediate to the longitudinal and transverse directions of the pipe, three pairs of transducers are arranged to transmit beams of ultrasonic energy into the pipe wall in an oblique clockwise direction at an angle of 12° with respect to the axis of the pipe. One transducer assembly of each pair is disposed to transmit in the clockwise forward direction while the other transducer assembly of the pair, positioned in a diametrically opposed location, is disposed to transmit in the clockwise reverse direction. All the forward transmitting transducers are mounted in a transducer holder 61 and all the reverse transmitting transducers are mounted in a transducer holder 62 which is positioned diametrically opposite the holder 61. The transducers, which transmit obliquely at an angle of 12° with respect to the pipe axis, are mounted in uniform spacing in the axial direction of the pipe and near one end of the generally elongate transducer shoe.

An additional group of three pairs of ultrasonic transducers are also provided for transmitting beams of ultrasonic energy obliquely and clockwise into the pipe well at an angle of 27° with respect to the pipe axis. As with the previous pairs of obliquely transmitting transducers, one transducer assembly of each pair is disposed to transmit in the forward clockwise direction whereas the other member of the pair transmits in the reverse clockwise direction. Another group of three pairs of forward and reverse transmitting transducers are provided for transmitting beams of ultrasonic energy obliquely and clockwise into the pipe wall at an angle of 42° with respect to the pipe axis. The forward transmitting transducer assembly of each pair are mounted in the transducer holder or shoe 61 and the reverse transmitting transducers are mounted in the transducer holder or shoe 62. The three pairs of axially spaced transducers in each group provide an effective scan length of .7 inch.

Since some flaws are liable to be substantially invisible to transducers whose beams are transmitted thereto in a clockwise direction of the pipe, additional transducers are provided for transmitting ultrasonic beams at an oblique relation to the pipe but in the counterclockwise direction. Similar to the arrangement of the clockwise transmitting transducers, the counterclockwise transmitting transducers are comprised of three groups, each group consisting of three pairs of transducer assemblies, with one group disposed to transmit at an angle of 12°, another group to transmit at 27°, and a third group to transmit at 42°. In each pair, one transducer assembly transmits in the forward counterclockwise direction and the other transducer, diametrically opposed thereto, is disposed to transmit in the reverse counterclockwise direction. All forward transmitting transducers of the three groups are mounted in a transducer shoe 71 and all reverse transmitting transducers of the three groups are mounted in a diametrically opposed transducer shoe 72.

Figure 5:
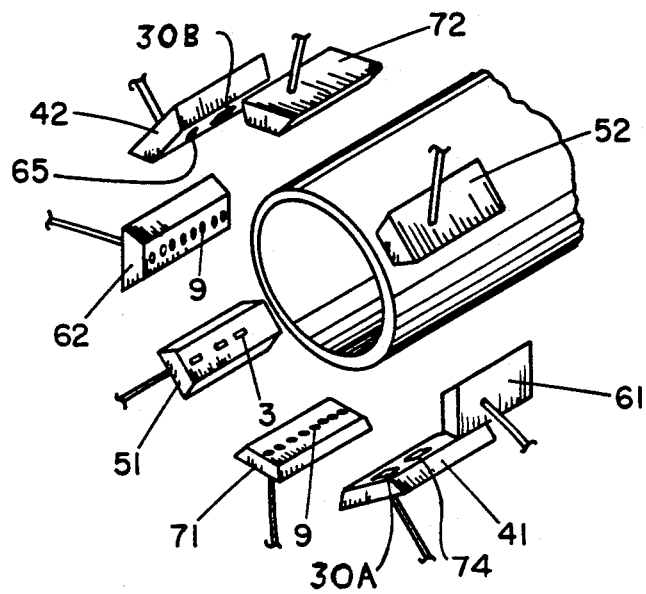
FIG. 5 is a fragmentary perspective view illustrating the orientation of the transducer holders of the invention.

Also mounted within the transducer shoe 41, in addition to the transducer 30A which is oriented for transmission of a sonic beam in the transverse clockwise direction of the pipe, is a wall thickness transducer 74 as shown in FIG. 5 which is adapted to generate ultrasonic wave energy which is coupled to the pipe and transmitted therein as compressional longitudinal waves of ultrasonic energy within the pipe wall to be reflected back to the transducer by the outer and inner surfaces of the pipe. As is well known, from observation of the transit times of the reflected sonic wave and the time interval between reflections, it is possible to determine the wall thickness of the pipe.

It is particularly important that the spacing of the transducers from the pipe surface be maintained. A variation in the transducer spacing from the pipe could result in a failure of the coupling medium, a water column, to couple sonic energy to the pipe or could alter the impacting location of the beam such that the pipe is inadequately scanned. Furthermore, the transit time of the reflected pulses of sonic energy, is critical to determining the location of flaws and variations in the spacing would lead to error. As the transducers are rotated about the pipe to be inspected, an out-of-round condition of the pipe or a bent pipe will cause the centerline of the transducer rotating assembly to be different from the pipe centerline and therefore cause a variation in the gap spacing of the transducers from the pipe surface unless the pipe is moved such that its centerline moves to a position of coincidence with the center of the transducer array so as to maintain uniform space. For this purpose, a proximity sensor 65 is mounted in the transducer holder 42 alongside the ultrasonic transducer for detecting longitudinal defects. A preferred form of proximity sensor is of the eddy current type where a probe coil is used to generate an alternating magnetic field and induce eddy currents in the surface of the test object. The secondary magnetic field produced by the circular pattern of the eddy currents produces variations in the impedance of the existing coil indicative of the proximity of the object.

A schematic of the control system for maintaining the gap between the transducer holders and the pipe, and accordingly the gap between the transducers and the pipe, is shown in FIGS. 4a and 4b. A proximity sensor 65 mounted in the transducer holder 42 provides an electrical signal by conventional means, typically including an impedance bridge, which signal is indicative of distance to the surface of the pipe. The proximity sensor signal is coupled as an input signal to a computer 66 via a conductor 67. In response thereto, the computer 66 is programmed to transmit output control signals to a centralizer control system 60 for maintaining the longitudinal axis of the pipe in coincidence with the central axis of the circular array of transducers. The control system 60 shown in FIG. 4a includes the four rollers 12, each of which is normally disposed in contact with the outside surface of the pipe in close proximity to the chuck 18, preferably such that the rollers of centralizer 60 are spaced less than six inches in the axial direction of the pipe from the chuck 18. The rollers 12 are arranged in pairs of diametrically opposed rollers with one roller of each pair being urged into contact with the pipe surface by an instrumented linear hydraulic actuator such as $I_1$ and the other roller of the pair being urged into contact with the pipe by a slave linear hydraulic actuator such as $S_1$ which is constantly pressurized by an appropriate source of hydraulic pressure (not shown) to urge its associated roller 12 against the pipe with a constant force. Each hydraulic actuator I includes an actuating element 68 which rotatably supports its associated roller 12 and is adapted to drive its roller 12 in a linear direction in response to an output signal from the computer 66 delivered thereto by means of conductor 69 which connects to actuator $I_1$ and conductor 70 which connects with actuator $I_2$. As shown in FIG. 4a, one pair of hydraulic actuators $S_1$ and $I_1$, and associated rollers 12 are arranged to bend the pipe in a direction which is orthogonal to the direction of bending controlled by the other pair of rollers and hydraulic actuators $S_2$ and $I_2$. A decrease in hydraulic pressure to actuator $I_1$ as controlled by the computer output signal allows the pipe to be bent upwardly as seen in FIG. 4a by the constant force exerted thereon by the slave actuator $S_1$ and its associated roller 12, whereas an increase in pressure to $I_1$ moves the pipe downwardly against the force applied by the actuator $S_1$. Actuators $S_2$ and $I_2$ function in similar manner. Thus, a variation in the distance signal from the proximity sensor 65 actuates the computer 66 to provide output signals for driving the hydraulic actuators $I_1$ and $I_2$ to bend the pipe P to a position wherein its central axis is maintained in coincidence with the center of the circular transducer array with an accuracy of approximately ten one thousandths inch.

For an inspection operation, the transducer holders are placed adjacent the surface of the pipe by operation of the chuck 18, wherein a chuck gear 77 engages gear teeth 76 affixed to the jaw J to move the jaw J towards or away from the pipe P. Each transducer holder is fixed to a jaw J by a bracket 78 and is pivotal thereon about a pivot 79 at the attachment of the bracket at one side of the transducer holder. The holder is moved from the dotted line position shown in FIG. 4c to its operative position by pressurization of a hydraulic cylinder 80 which pivotally connects to the holder on the side thereof opposite pivot 79 and also to the jaw J.

Each transducer holder is mounted to a different jaw J and provided with its own hydraulic cylinder 80. The cylinders 80 are pressurized by a pump 93 mounted in the chuck housing as shown in FIG. 1 in a hydraulic system with a fluid reservoir (not shown). The pump shaft is connected through a gear 94 with a gear 95 on the barrel 20. When chuck 18 is spun by the motor 21 at a rate faster than the rotation of the barrel 20, the pump action is increased to pressurize each of the cylinders 80 and pivot the transducer holders to their operative scanning position as shown in FIG. 4c. When the chuck rotational speed controlled by motor 21 is less than that of barrel 20, the pump ceases to pressurize the cylinders 80 and each of the transducer holders is retracted away from the pipe to a position as shown in dotted lines. When the chuck 18 and barrel 20 rotate at equal speeds, the transducer holders maintain their position relative to the pipe P.

Figure 6:
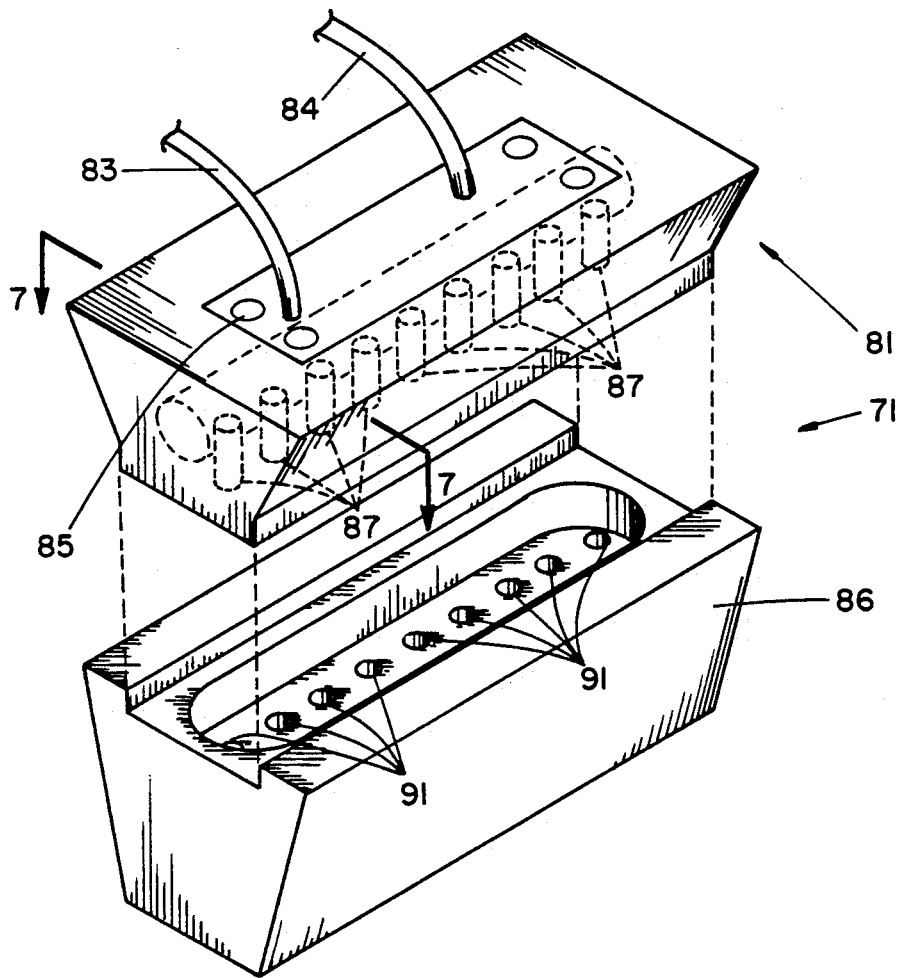
FIG. 6 is an exploded view in perspective of a transducer holder for ultrasonic transducers which are disposed to transmit pulses of ultrasonic energy into a pipe wall at angles oblique to the longitudinal axis of a pipe to be inspected.
Figure 7:
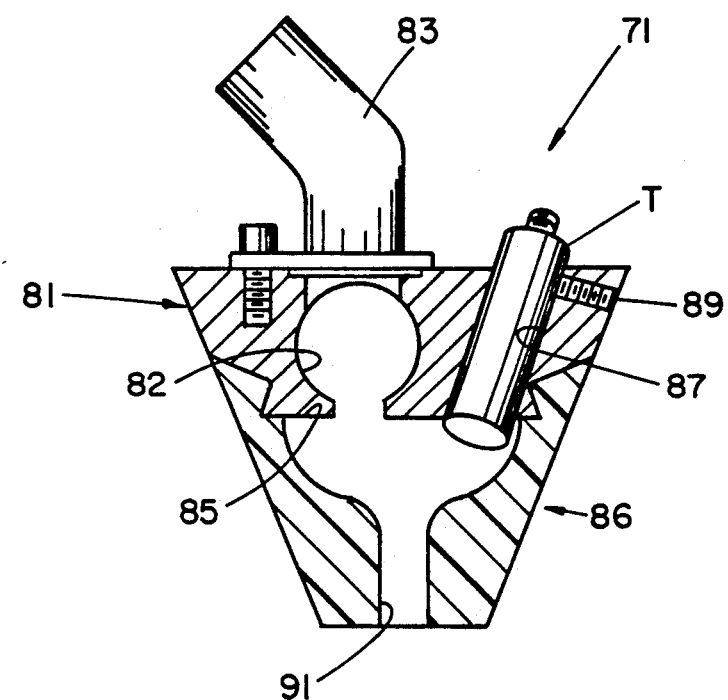
FIG. 7 is a cross section of the transducer holder of FIG. 6 when assembled as taken along the section line 7-7 in the base member of the transducer holder FIG. 6, but showing one of the transducers mounted therein.
Figure 8:
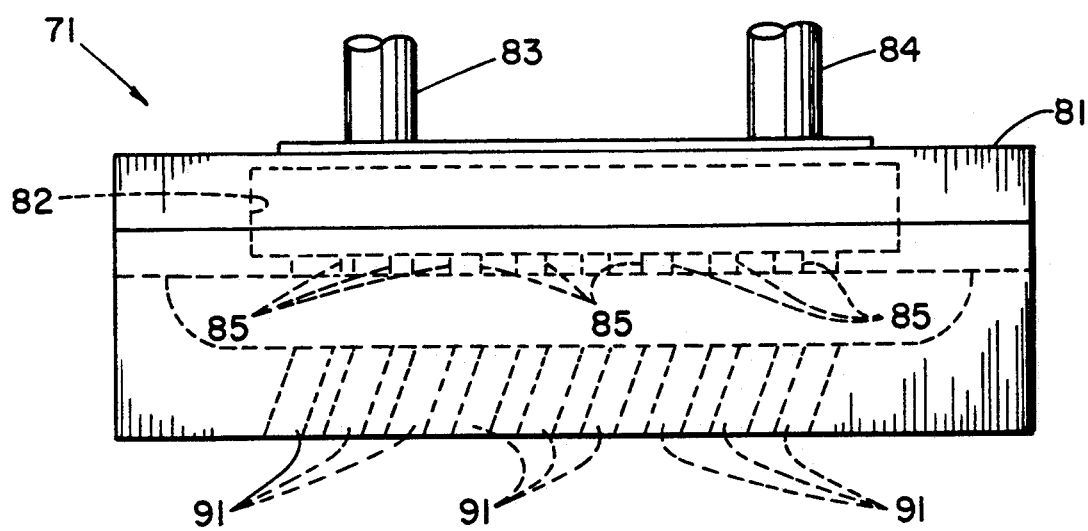
FIG. 8 is a longitudinal cross section of the transducer holder of FIG. 6.

A transducer holder 71 in which nine ultrasonic transducers are mounted is shown in FIGS. 6, 7 and 8. The transducer holder 71, which carries transducers for transmitting pulsed beams of some energy in oblique directions with respect to the pipe axis, comprises an elongate metallic base member 81, of generally trapezoidal cross section. The base member 81 is formed with an elongate bore 82 extending lengthwise of the base member and parallel to its longitudinal axis. The bore 82 is adapted to serve as a conduit or receive a conduit therein which is connected to a pair of water supply lines 83, 84 connecting thereto at the top side of the base member. The conduit is also provided with nine axially spaced openings 85 opposite the supply lines 83, 84 for delivering water to a trough-like member 86 affixed to the underside of the base member. Nine openings or bores 87 are also formed in the base member 81 to extend therethrough at an angle of 18° with respect to a vertical axis of the base member as seen in FIG. 7 which is also disposed radially of the axis of the pipe when the transducer holder is positioned in operational proximity thereto. The nine bores comprise three groups of three bores each, in one group of which each is directed at an angle of 12° with respect to the longitudinal axis of the base member, another group directed at an angle of 27° with respect to the longitudinal axis of the base member, and a third group, each of which is directed at an angle of 42° to the longitudinal axis.

The nine bores 87 are each dimensioned to snugly receive an ultrasonic transducer T which is clamped in fixed position therein by means of a set screw 89.

The trough 86, which is of urethane material, includes a pair of upwardly extending flanges which extend the length of the trough at opposite sides thereof and are adapted to clamp to the underside of the base member 81. The trough 86 is disposed to receive water from the conduit 82 and dispense water in columns through nine openings 91 disposed in alignment with the transducers T and thereby provide a medium for coupling sonic energy to a pipe or test object to be inspected. Each of the nine openings 91 is in the form of a venturi nozzle which reduces turbulence in the water column dispensing therethrough.

The transducer holder 71 is fixed to one of the jaws of the eight jaw chuck 18 which is driven by one of the hydraulic cylinders 80. In operation it is held a fixed distance, such as ⅛ inch, from the surface of the pipe and is disposed to extend in the longitudinal direction of the pipe to be inspected. All of the transducer holders 71, 72, 61, 62 are similarly formed. However, the holders 51 and 52 utilized for the detection of transverse flaws are provided with only three bores for accommodating three transducers, but are otherwise similar to the transducer holders 71. The holders 41 and 42 each include a bore and water column opening for accommodating a transducer which transmits in the transverse direction of the pipe. The holder 41, however, further includes a radially extending bore for accommodating a wall thickness transducer and a water column opening aligned therewith. Construction is otherwise similar to the transducer holder 71.

Figure 9:
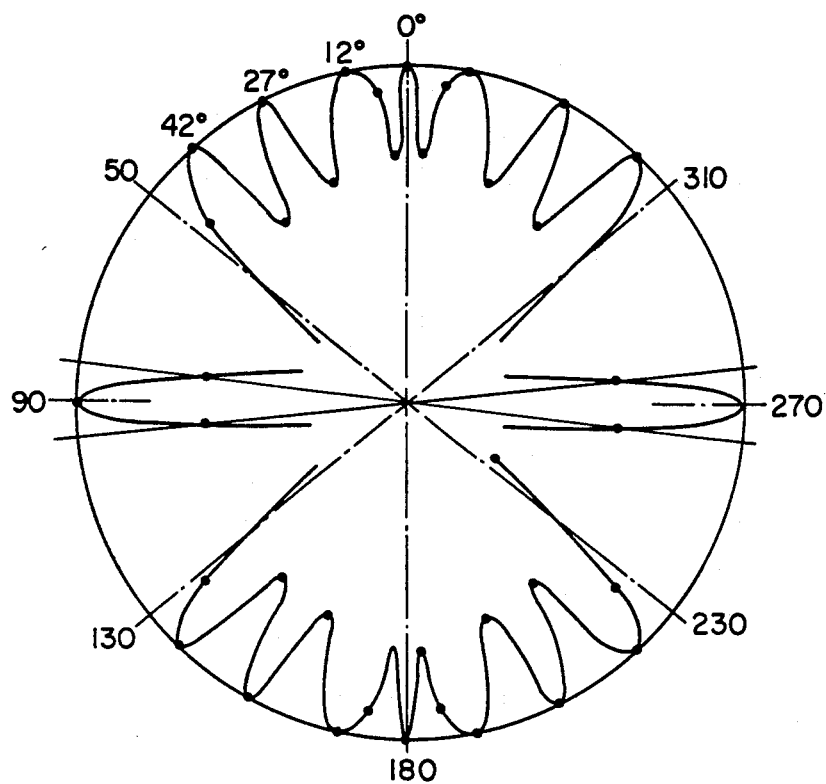
FIG. 9 is a schematic circular plot of pipe inspection responses of the transducer array of the invention.

FIG. 9 is a sample schematic circular plot or inspection footprint of transducer response to flaws in a pipe wall which extend therein at a variety of angles to the axis of the pipe. Transducer response for transducers arrayed in accordance with the invention is represented by a dashed line which varies generally sinusoidally from a 100% maximum at the outer circle to a reduced 70% response level, 3 decibel down from the maximum as represented by the inner circle. The inclination of the transducers, 18° from the perpendicular to the pipe surface, produced a 42° shear wave angle with respect to the radial direction of the pipe which provided an optimum response for the transducers transmitting obliquely at angles of 12°, 27° and 42° to the axis of the pipe as well as those transmitting in the longitudinal, 0° direction, or transversely at 90°. Flaws extending at these angles with respect to the pipe axis produced maximum reflection responses as indicated by the small dots on the outer response circle. Flaws extending at angles intermediate these angular directions, produced reduced responses as low as the −3db level for those at mid-points in between. Flaws very close to the 12°, 27° and 42° directions produced slightly less than maximum responses. The apparatus is also shown to be sensitive, i.e., producing greater than 70% response levels, to transverse flaws extending 90° transverse to the pipe axis or within the range of 82° to 98° centered about the 90° transverse direction. The apparatus was blind to flaws extending obliquely in the ranges of 50° to 82°, 98° to 130°, 230° to 262°, and 278° to 310°. To obtain usable reliable responses above the 70% response level for these ranges, additional oblique transmitting transducers must be provided.

The piezoelectric transducers of the invention are energized periodically to transmit pulses of ultrasonic energy into the tubular member to be inspected. The sonic wave is reflected between the inner and outer surfaces and if it should encounter a discontinuity, the wave will be reflected back to the transmitting transducer. In order to sense the reflected wave and produce an electrical response, the transducer must be in a de-energized state. Accordingly, each transducer is de-energized after a pulse transmission and the apparatus appropriately gated to respond to reflections from flaws in both the inner diameter and outer diameter surfaces.

All the forward transmitting transducers along with the wall thickness transducer are pulsed to transmit simultaneously at the rate of 5000 pulses per second. All the reverse transmitting transducers are pulsed to transmit 100 microseconds after the pulsing of the forward transmitting transducers.

The inner barrel 20 and attached transducers are rotated at a selected speed of rotation in the range of 250 to 500 r.p.m. By the use of linearly spaced transducers in the groups of transducers for detecting oblique and transverse oriented flaws, a .7 inch axial scan coverage of the pipe surface is obtained for each revolution. Accordingly, it is possible to completely scan 14.58 axial feet of pipe per minute without overlap at 250 r.p.m. By slowing the axial speed, it is possible to obtain an overlap. For example, a 20% overlap of scan coverage can be obtained with an axial speed of pipe of 11.7 ft. per minute.

Figure 10:
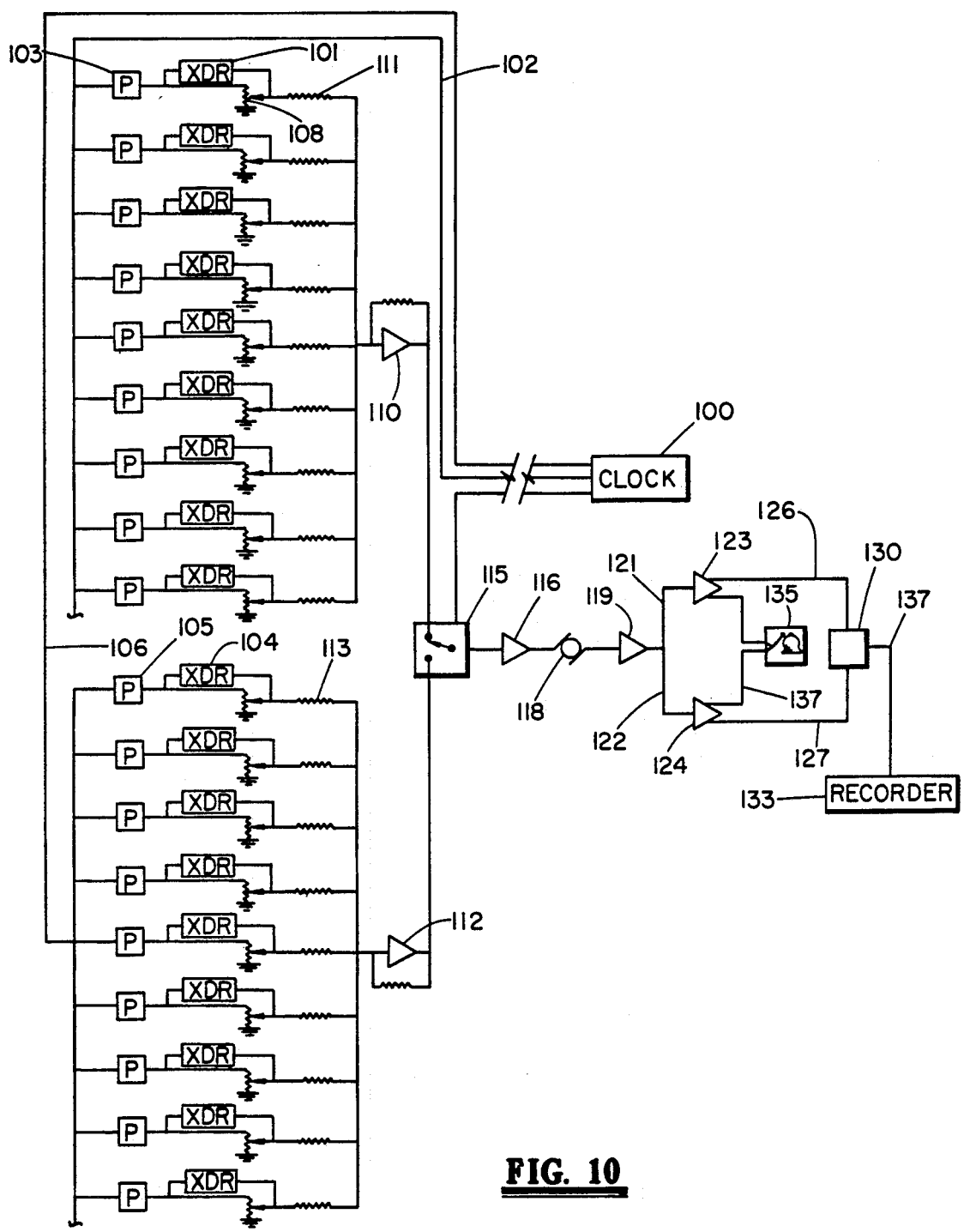
FIG. 10 is an electrical schematic and block diagram of the electrical system of the invention for operation of an array of ultrasonic transducers mounted in a pair of diametrically opposed transducer holders for transmitting pulsed beams of ultrasonic energy into a pipe wall at angles oblique to its longitudinal axis.

The system for detection of flaws which are obliquely oriented with respect to the pipe axis is shown schematically in FIG. 10. The system is shown for two banks of ultrasonic transducers, in the first bank of which nine transducers 101 are mounted in the transducer holder 71 and are disposed to transmit in a forward and counter-clockwise direction. Another nine transducers 104 are mounted in the transducer holder 72 and are disposed to transmit in the reverse counterclockwise direction. The system is controlled by a 10,000 cycle per second clock 100 which activates the nine pulsers 103 through a conductor 102 by delivering voltage pulses every 200 microseconds to repeatedly and simultaneously fire each of the forward transmitting transducers 101. After each activation of the pulsers 103, the nine pulsers 105 are activated by clock purses via conductor 106 to deliver voltage pulses every 200 microseconds to repeatedly and simultaneously fire each of the reverse transmitting transducers 104. Connected in parallel with each of the transducers 101 is a variable resistance 108 which is connected to the pulser output to permit adjusting and equalizing the response of the transducers 101. A similar variable resistance 109 is provided to adjust the response of each transducer 104. The outputs of each of the transducers 101 are summed by a summing amplifier 110 with associated summing resisters 111 and a summing amplifier 112 with associated summing resistors 113 is provided to sum the responses of the transducers 104. An electronic switch 115 controlled by the clock 100 alternately connects with the respective amplifiers 110 and 112 every 100 microseconds to sequentially deliver their outputs to a driver amplifier 116, the output of which is delivered by a slip ring connection 118 to an amplifier 119. The switch 115 is controlled such that as the clock energizes the first bank of transducers, it also places the switch in a first position (or state) to "listen" for their response. As it next energizes the second bank of transducers, it also moves the switch to a second position (or state) to "listen" for a response from the second bank.

The amplified output from amplifier 119 is delivered by respective conductors 121, 122 to a pair of electronic gates 123,124. The gate 123 is opened for signals representing the reflections of sonic pulses from flaws located on the inner surface of the pipe while the gate 124 is opened for the reception of signals representing the reflections of sonic pulses from flaws on the outer diameter surface of the pipe. The gates 123,124 are each coupled to a smoothing filter 130 by conductors 126,127 respectively to filter the gate outputs. The filter output is then coupled to an appropriate recorder mechanism 133 by a conductor 132. In addition to the visual or magnetic recording of flaw detector pulses by the recorder 133, an audible alarm for signaling detection of a flaw is provided by a bell 135 which is activated by an output from either of the gates 123,124 which exceeds a predetermined threshold. The gates are coupled to the alarm bell 135 by coupling conductors 136,137 respectively.

It is to be understood that the system for control of the transducers mounted in transducer holders 61 and 62 and which are disposed to transmit obliquely but clockwise in the forward and reverse directions is substantially identical to the system shown in FIG. 10. All the forward transmitting transducers in the transducer holder 71 are fired simultaneously with those in transducer holder 61, receiving their activating clock pulses over the same conductor 102. In like manner, all reverse transmitting transducers, mounted in transducer holders 72 and 62 respectively, are fired simultaneously by clock pulses delivered via conductor 106.

Figure 11:
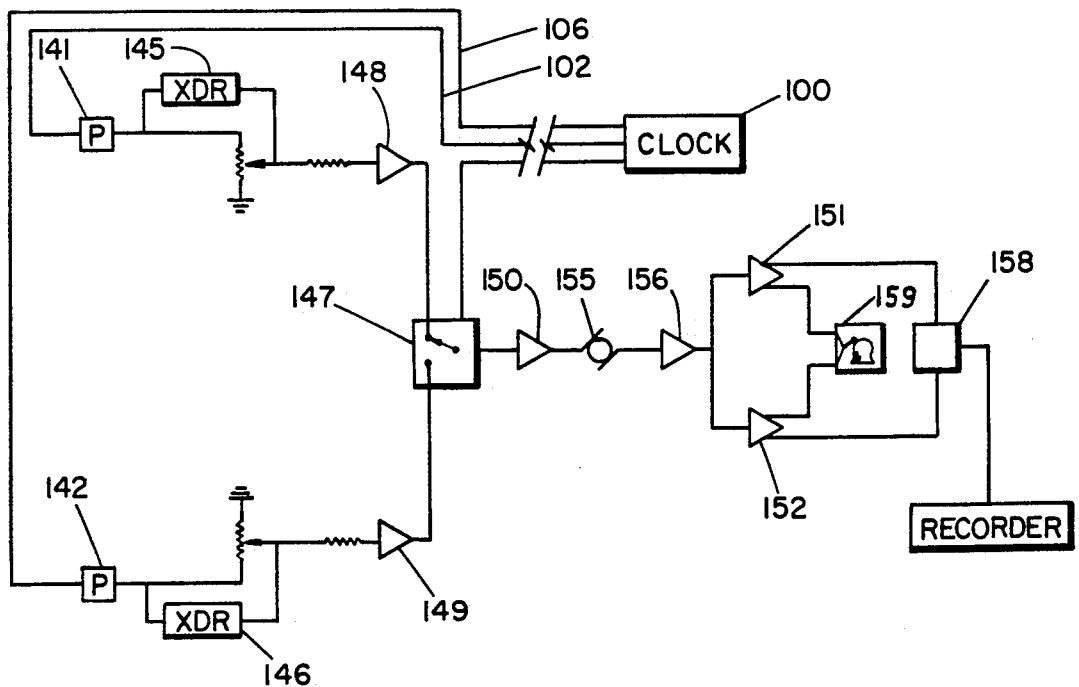
FIG. 11 is an electrical schematic and block diagram of the electrical system of the invention for operation of a pair of ultrasonic transducers mounted in a pair of diametrically opposed transducer holders for transmitting pulsed beams of ultrasonic energy into a pipe wall in transverse directions therein for the detection of longitudinal defects.

The system for detection of longitudinal flaws is shown in FIG. 11. Clock pulses are delivered by conductors 102 and 106 to activate pulsers 141,142 respectively, which periodically energize the transducers 145,146 whose responses to sonic reflection signals are amplified by amplifiers 148,149 respectively, and coupled to an electronic switch 147. The switch 147 alternately connects the amplified outputs of transducers 148,149 to a driver amplifier 150 whose output in turn is delivered to a pair of gates 151,152 via a slip ring connection 155 and amplifier 156. The gates 151,152 are opened to receive signals indicative of flaws detected on the inner diameter and outer diameter surfaces of the pipe, respectively. The gate outputs are coupled to a smoothing filter 158 prior to recording in the recorder 133. An alarm bell 159 is also coupled to the gate outputs to signal detection of a flaw when the output signal exceeds a predetermined threshold.

Figure 12:
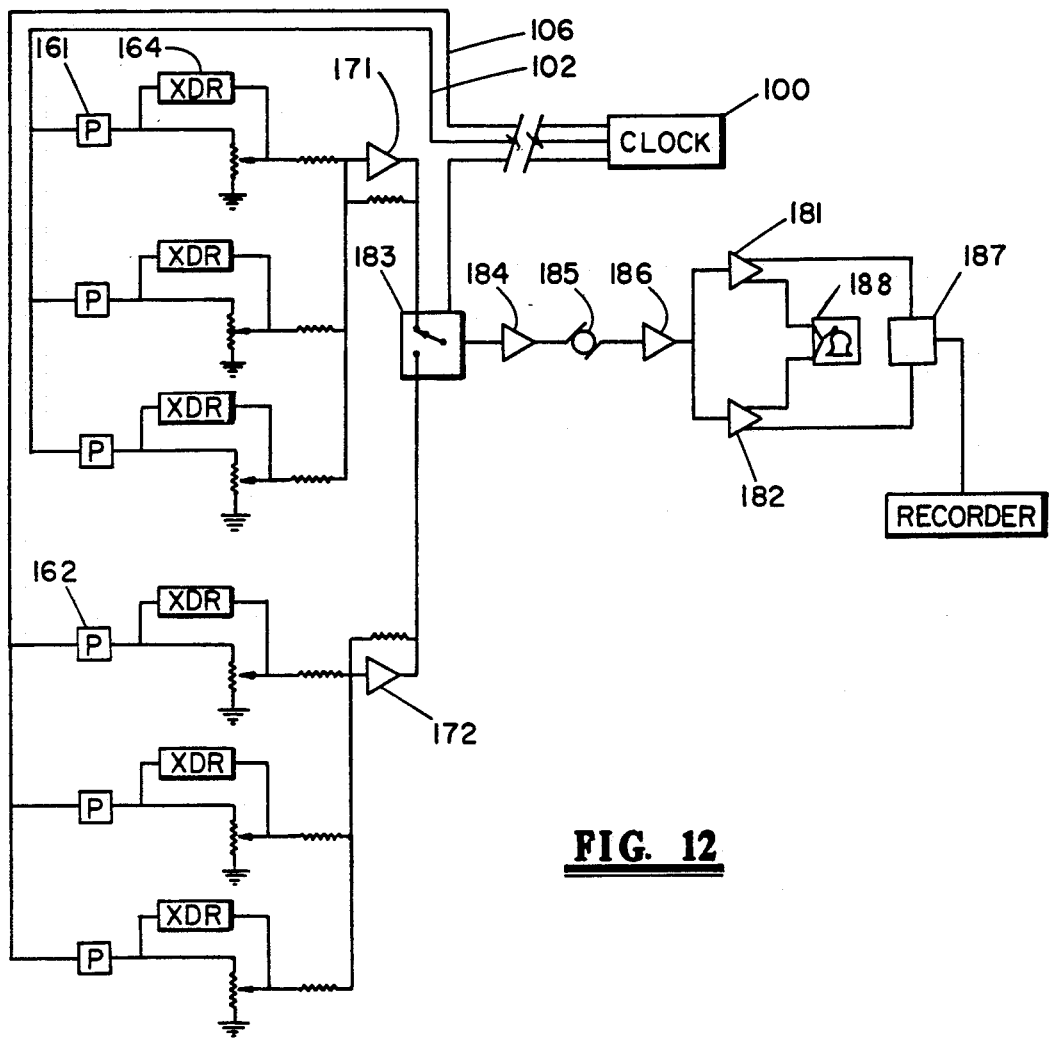
FIG. 12 is an electrical schematic and block diagram of the electrical system of the invention for operation of ultrasonic transducers for transmitting pulsed beams of ultrasonic energy into a pipe wall for the detection of defects which extend transversely therein.

The detection system for detection of transverse flaws is shown schematically in FIG. 12. In this system the clock 100 delivers its clock pulses over conductors 102,106 to pulsers 161,162 respectively. The forward transmitting transducers 164 mounted in transducer holder 51 are energized by the pulsers 161 and the reverse transmitting transducers 166 mounted in transducer holder 52 are energized by the pulsers 162. The reflection response outputs of transducers 164 are summed in a summing amplifier 171 and outputs of transducers 166 are summed in summing amplifier 172. The summed outputs from the forward and reverse transmitting transducers are delivered to a pair of gates 181,182 via an electronic switch 183 controlled by clock 100, a driver amplifier 184, slip-ring connection 185, and amplifier 186. The gates 181,182 which are operative to receive reflections from the inner and outer diameter pipe surfaces, are coupled to deliver their outputs to a smoothing filter 187 prior to recording by recorder 133. A threshold audible alarm 188 is also coupled to the gate outputs.

Figure 13:
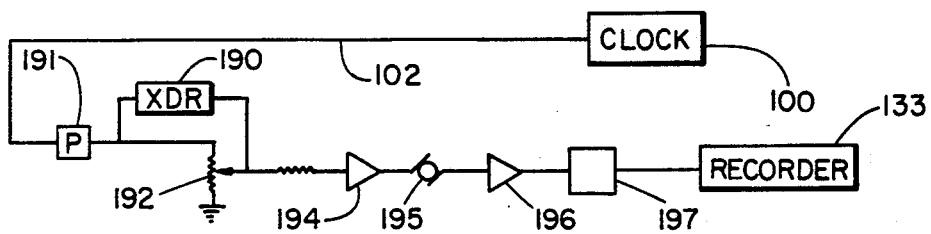
FIG. 13 is an electrical schematic and block diagram of the electrical control system of the invention for operation of a wall thickness transducer of the invention.

The system for wall thickness detection is shown in FIG. 13. The wall thickness transducer 190 is energized by a pulser 191 which receives clock pulses over the conductor 102. The wall thickness transducer is fired to transmit simultaneously with all forward firing transducers. The transducer response is adjusted by a variable resistance 192. The reflection response of the transducer 190 is delivered to an amplifier 194, whose output is coupled to the recorder 133 via a slip-ring connection 195, amplifier 196 and a time-to-wall thickness converter 197.

Figure 14:
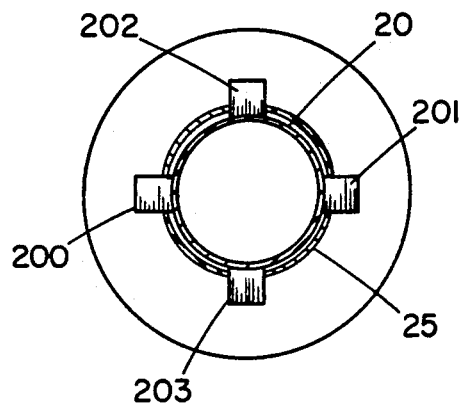
FIG. 14 is a view taken along the section line 14-14 in FIG. 1 to show the mounting of amplifier, pulser, and power supply boxes for the flaw detection systems of the invention.

Electronic component boxes for the several detection systems are shown in FIGS. 1 and 14 wherein power supply boxes 200,201 are shown attached to the rotatable barrel 20 in diametrically opposed locations. An amplifier box 202 and pulser box 203 are also attached to the barrel 20 in opposed locations thereon. A slip-ring connection assembly 206 is also provided in circumferential relationship about the barrel 20 and includes the slip-ring connections 118,115,185, 195.

It is therefore to be seen that the unique ultrasonic inspection apparatus described herein permits a more efficient and precise inspection of tubular members than has heretofore been obtained. The use of multiple pairs of transducers disposed in linear, axial array for transmitting in each of the longitudinal and plurality of oblique directions greatly increases the scan coverage for each revolution of transducers and therefore reduces the time required for an inspection. The electronic system for rapidly and repeatedly energizing the transducers and switching to alternately couple the transducer responses to a recorder means allows for a time efficient operation without a need for multiplexing.

In addition, provision of a separate pulser as an excitation means for each transducer provides for a very good signal-to-noise ratio. Furthermore, the provision of an automatic control means for maintaining the transducers a closely controlled precise distance from the outer surface of the tubular member minimizes the variation in spacing between the transducers and the pipe surface as well as the angle of the transducers relative to the surface to a greater degree than has been possible with the prior art devices. Maintaining a precise distance and orientation of the transducers to the tubular member is critical to sonic coupling as well as obtaining a reliable determination of the location and extent of structural flaws.

It is also to be understood that the foregoing description of a preferred embodiment of the invention has been presented for purposes of illustration and is not intended to limit the invention to the precise form disclosed. For example, the oblique transducers could be disposed to transmit at angles other than 12°, 27° and 42°. It is to be appreciated therefore, that various changes may be made in the invention without departing from the spirit of the invention.

We claim:

1. An apparatus for positioning devices for the transmission of acoustic energy in non-contacting fixed spaced relation to the outer diameter surface of a tubular member in a procedure for the non-destructive testing and inspection of the tubular member, said apparatus comprising:

a plurality of contact elements comprising at least two pairs of rollers in which the rollers of each pair are disposed in contact with the outer surface of the tubular member in alignment with each other and the central axis of the tubular member in diametrically opposed positions relative thereto and said pairs of rollers are disposed and aligned in mutual orthogonal relationship, a proximity sensor for sensing the distance of said devices from the tubular member and generating an electrical signal corresponding to said sensed distance, and driving means responsive to said proximity sensor signal for driving the rollers of each pair in a linear radial direction with respect to said tubular member axis whereby the axis is moved to coincidence with the center of the circular array of transmitting devices.

2. An apparatus as set forth in claim 1 wherein said driving means includes computer means responsive to said sensor signal for generating output centering control signals and master and slave actuator devices associated with each of said pair of rollers responsive to said control signals for driving the diametrically opposed rollers of the pair in linear radial movement with respect to the central axis of the tubular member whereby the tubular member is deflected as necessary to maintain its axis in coincidence with the center of the circular array of transmitting devices and therefore maintain the transmitting devices a fixed distance from the outer surface of the tubular member as the tubular member is ultrasonically scanned.

3. An apparatus as set forth in claim 1 wherein said devices are a plurality of ultra-sonic transducers arranged in circular array about the tubular member and positioned to transmit beams of sonic energy through a sonic coupling medium into the wall of the tubular member and to receive reflections thereof.

4. An apparatus as set forth in claim 1 wherein said proximity sensor comprises an eddy current probe for generating a magnetic field and inducing currents in the tubular member, and means responsive to said induced currents for deriving an electrical signal representing the distance between said devices and the outer surface of the tubular member.

5. An ultrasonic inspection apparatus for the nondestructive inspection of cylindrical tubular members, said apparatus comprising:

means for transmitting beams of pulsed sonic wave energy into the wall of the tubular member wherein each of said beams is refracted to propagate shear wave energy in a path at an angle of approximately 42° with respect to the radial direction of the tubular member, said means comprising a pair of ultrasonic transducers disposed to transmit in opposite transverse directions with respect to the tubular member for the detection of flaws which extend in the longitudinal direction of the tubular member, a plurality of pairs of ultrasonic transducers disposed to transmit in the longitudinal direction of the tubular member for the detection of transverse flaws wherein one transducer of each longitudinal transmitting pair transmits in the forward longitudinal direction and the other transducer of the pair transmits in the reverse longitudinal direction, a plurality of pairs of ultrasonic transducers disposed to transmit pulsed beams of sonic shear wave energy in directions oblique and clockwise with respect to the longitudinal axis of the tubular member for the detection of flaws which extend obliquely with respect too said tubular member axis and wherein one transducer assembly of each oblique flaw detecting pair is disposed to transmit in the forward clockwise direction and the other transducer assembly of each oblique flaw detecting pair is disposed to transmit in the reverse clockwise direction, a plurality of pairs of ultrasonic transducers disposed to transmit pulsed beams of sonic shear wave energy in directions oblique and counterclockwise with respect to the longitudinal axis of the tubular member for the detection of flaws which extend obliquely with respect to said tubular member axis and wherein one transducer assembly of each oblique flaw detecting pair is disposed to transmit in the forward counterclockwise direction and the other transducer assembly of each oblique flaw detecting pair is disposed to transmit in the reverse counterclockwise direction, means for effecting relative movement between said tubular member and all of said transducers such that said transducers are moved in a helical scanning path relative to said tubular member, means for simultaneously and repetitively energizing and de-energizing all of the forward transmitting transducers to transmit pulsed beams of sonic energy to the tubular member and to receive shear wave energy reflections thereof and after each such transmission simultaneously and repetitively energizing and de-energizing all of the reverse transmitting transducers to transmit pulsed beams of sonic energy to the tubular member and to receive reflections thereof, means for positioning each of aid transducers in non-contacting fixed spaced relation to the outer diameter surface of the tubular member and in circular array thereabout, said positioning means comprising at least two pairs of contact members in which the contact members of each pair are disposed in contact with the outer surface of the tubular member in alignment with each other and the central axis of the tubular member in diametrically opposed positions relative thereto, a proximity sensor for sensing the distance of said transducers from the tubular member and generating an electrical signal corresponding to said sensed distance, driving means responsive to said proximity sensor signal for driving the contact members of each pair in a linear radial direction with respect to said tubular member axis whereby the axis is moved to coincidence with the center of the circular array of transmitting devices, and means for sonically coupling each transducer to the tubular member by a flowing column of a liquid medium.

6. An ultrasonic inspection apparatus for the nondestructive inspection of cylindrical tubular members, said apparatus comprising:

means for transmitting beams of pulsed sonic wave energy into the wall of the tubular member wherein each of said beams is refracted to propagate shear wave energy in a path at an angle of approximately 42° with respect to the radial direction of the tubular member, said means comprising a pair of ultrasonic transducers disposed to transmit in opposite transverse directions with respect to the tubular member for the detection of flaws which extend in the longitudinal direction of the tubular member, a plurality of pairs of ultrasonic transducers disposed to transmit in the longitudinal direction of the tubular member for the detection of transverse flaws wherein one transducer of each longitudinal transmitting pair transmits in the forward longitudinal direction and the other transducer of the pair transmits inn the reverse longitudinal direction, a plurality of pairs of ultrasonic transducers disposed to transmit pulsed beams of sonic shear wave energy in directions oblique and clockwise with respect to the longitudinal axis of the tubular member for the detection of flaws which extend obliquely with respect to said tubular member axis and wherein one transducer assembly of each oblique flaw detecting pair is disposed to transmit in the forward clockwise direction and the other transducer assembly of each oblique flaw detecting pair is disposed to transmit in the reverse clockwise direction, a plurality of pairs of ultrasonic transducers disposed to transmit pulsed beams of sonic shear wave energy in directions oblique and counterclockwise with respect to the longitudinal axis of the tubular member for the detection of flaws which extend obliquely with respect to said tubular member axis and wherein one transducer assembly of each oblique flaw detecting pair is disposed to transmit in the forward counterclockwise direction and the other transducer assembly of each oblique flaw detecting pair is disposed to transmit in the reverse counterclockwise direction, means for effecting relative movement between said tubular member and all of said transducers such that said transducers are moved in a helical scanning path relative to said tubular member, means for simultaneously and repetitively energizing and de-energizing all of the forward transmitting transducers to transmit pulsed beams of sonic energy to the tubular member and to receive shear wave energy reflections thereof and after each such transmission simultaneously and repetitively energizing and de-energizing all of the reverse transmitting transducers to transmit pulsed beams of sonic energy to the tubular member and to receive reflections thereof, means for supporting each of said transducers in non-contacting fixed spaced relation to the outer diameter surface of the tubular members, means for sonically coupling each transducer to the tubular member by a flowing column of a liquid medium, said means for supporting the transducers including an annular support member, said transducers being mounted on said annular support member in circular array about the central axis of the annular support member with the transducers in each pair being disposed in diametrically opposed positions with respect to the axis of the annular support member, and wherein said means for effecting relative movement includes:

means for moving the tubular member to be inspected in its longitudinally axial direction through the circular array of transducers in substantially concentric relation therewith, means for rotating said annular support member and transducer arrays about the central axes of the support member and the tubular member as said tubular member is moved past said transducer arrays, positioning means for automatically maintaining each of said transducers a predetermined fixed optimum distance from the surface of aid tubular member as said transducer arrays are rotated thereabout, said positioning means including a proximity sensor for sensing the distance of one of said transducers from the outer diameter surface of the tubular member and generating an electrical signal corresponding to said sensed distance, a plurality of contact elements comprising at least two pairs of rollers in which the rollers of each pair are disposed in contact with the outer surface f the tubular member in alignment with each other and the central axis of the tubular member in diametrically opposed positions relative thereto and said pairs of rollers are disposed and aligned in substantially mutual orthogonal relationship, driving means responsive to said proximity sensor signal for driving the rollers of each pair in a linear radial direction with respect to said tubular member axis whereby the axis is moved to coincidence with the center of the circular array of transducers, said driving means including computer means responsive to said sensor signal for generating output centering control signals and master and slave actuator devices associated with each of said pair of rollers responsive to said control signals for driving the diametrically opposed rollers of the pair in linear radial movement with respect to the central axis of the tubular member whereby the tubular member is deflected as necessary to maintain its axis in coincidence with the center of the circular array of transducers and therefore maintain the transducers a fixed distance from the outer surface of the tubular member as the tubular member is ultrasonically scanned.

* * * * *